United States Patent [19]

Iacobelli

[11] Patent Number: 5,298,391
[45] Date of Patent: Mar. 29, 1994

[54] USE OF THE SP-2 MONOCLONAL ANTIBODY FOR THE CLINICAL DIAGNOSTICS AND FOR THE MONITORING OF THE HIV INFECTION PROGRESS

[75] Inventor: Stefano Iacobelli, Rome, Italy

[73] Assignee: Consiglio Nazionale Delle Ricerche, Rome, Italy

[21] Appl. No.: 688,312

[22] Filed: Apr. 22, 1991

[30] Foreign Application Priority Data

Apr. 23, 1990 [IT]  Italy ............................. 20113 A/90
Apr. 17, 1991 [EP]  European Pat. Off. ........ 91830153.2

[51] Int. Cl.$^5$ ............................................. C12Q 1/70
[52] U.S. Cl. ........................................ 435/5; 435/7.1; 435/7.92; 435/974; 530/322
[58] Field of Search .............. 435/5, 7.1, 7.92, 974; 530/322

[56] References Cited

U.S. PATENT DOCUMENTS 4,725,669  2/1988  Essex et al. ...................... 530/322

OTHER PUBLICATIONS

Iacobelli et al: "Detection of Antigens Recognized by a Novel MAb in Tissue and Serum from Patients with Breast Cancer" Cancer Res. 46, 3005–10 Jun. 1986.

*Primary Examiner*—Christine M. Nucker
*Assistant Examiner*—Jeffrey Stucker
*Attorney, Agent, or Firm*—Pollock, Vande Sande & Priddy

[57] ABSTRACT

A method for in vitro immunoassaying an antigen from biological fluids or tissues. The antigen is present in individuals infected with the AIDS virus. The antigen is of cytoplasmic origin and is recognized by an SP-2 monoclonal antibody produced by a hybridoma cell line deposited at the Collection Nationale de Cultures de Microorganisms, Accession, No. I-1083. The method comprises the steps of taking a sample of biological fluid or tissue from a person; contacting the biological fluids or tissues with the antibody; removing an amount of the antibody not binding with the antigen; and determining the amount of the antibody bound with the antigen utilizing at least one revealing system selected from the group consisting of enzyme, radioisotope, and chemiluminescent labels.

3 Claims, No Drawings

USE OF THE SP-2 MONOCLONAL ANTIBODY FOR THE CLINICAL DIAGNOSTICS AND FOR THE MONITORING OF THE HIV INFECTION PROGRESS

FIELD OF THE INVENTION

This invention relates to the use of SP-2 monoclonal antibody for the clinical diagnostics and for the monitoring of the progress of the HIV (human immunodeficiency virus) infection as well as in the production of kits for carrying out said diagnostic and monitoring analysis.

BACKGROUND OF THE INVENTION

It is well known that the SP-2 monoclonal antibody (IgG1 subclass) reacts with an antigen of 90,000 dalton molecular weight, not yet fully characterized and designated as 90 KD. This antigen has a cytoplasmic localization and is found tumoral tissue and in the sera of patients suffering from breast cancer and other neoplastic diseases (S. Iacobelli et al.; Cancer Research 46, 3005-10, 1986; Anticancer Research 8, 761-4, 1988; Breast Cancer Research and Treatment 11, 19-30, 1988; Gynecologic Oncology, 35, 286-9, 1989).

Now, it has been surprisingly found that the 90 KD antigen is also present in the sera of patients infected with HIV. Additionally, it has been found that the positivity percentage and the average antigen concentrations in serum are proportional to the extent of the infection, with increasing values on passing from the HIV-seropositivity conditions in asymptomatic subjects to the ARC (AIDS related complex) and to the AIDS (acquired immunodeficiency syndrome). Furthermore 90 KD antigen levels higher than those in normal subjects are found in the serum of anti-HIV seronegative subjects at high risk of HIV infection. The assay of the 90K antigen is performed by utilizing the monoclonal antibody SP-2, purified from the correspondent hybridoma cell line, deposited at DSM DEUTSCHE SAMMLUNG VON MIKROORGANISMEN UND ZELLKULTUREN GmbH under the Budapest Treaty under the accession number DSM ACC2116, Mascheroder Weg 1 B D-3300 Braunschweig, Germany, and at C.N.C.M. the Collection Nationale de Cultures de Microorganismes at the Pasteur Institute, Paris, France, under the accession number I-1083, as previously described by the present inventor, Iacobelli et al., 1986, Cancer Research, 46, 3005-3010 and Iacobelli et al., 1988, Breast Cancer Research and Treatment, 11, 19-30. The assay thus represents a very useful support for the early diagnosis of the HIV infection just before the patient shows the symptoms of the disease and for the monitoring of the progress of the infection itself. Accordingly, the test can be employed for selecting the patients who are to be treated therapeutically, and then for evaluating the efficacy of the treatment itself.

SUMMARY OF THE INVENTION

Thus it is an object of the present invention the use of the SP-2 monoclonal antibody for an in vitro assay of the 90K antigen from biological fluids or tissues useful for the clinical diagnostics related to HIV infection.

DETAILED DESCRIPTION OF THE PREFERRED EMBODIMENTS

Preferably the in vitro assay of the present invention of the 90K antigen is performed to make a diagnosis of the disease stage during the HIV infection, to foresee the evolution of the infection through ARC or AIDS in anti-HIV seropositive asymptomatic subjects, to monitor the progress of HIV infection, to evaluate the efficacy of a specific (antiviral) or aspecif therapy, early and/or to provide an indicator of the serum-conversion of anti-HIV seronegative subjects at risk.

According to the present invention, the in vitro assay is performed through immunoassays. The immunoassays used according to the present invention preferably utilize enzymatic, radioisotopic and/or chemiluminescent revealing systems. The enzymatic systems employed may include ELISA and/or EIA assays; the radio isotopic systems utilized may include IRMA and/or RIA systems.

The present invention also includes the use of the SP-2 monoclonal antibody for the preparation of diagnostic kits to perform the above described in vitro assays.

The diagnostic kits may preferably be used to perform the present invention in vitro assays where the threshold value of the 90 KD antigen in biological fluids or tissues is comprised between 9 and 13 U/ml.

The present invention will be described with refer to the following example:

EXAMPLE 1

A kit for the clinical diagnostics and the monitoring of the progress of the HIV infection including

| | |
|---|---|
| small polystyrene beads sensitized with SP-2 mouse monoclonal IgG | No. 100 |
| a tracer consisting of SP-2 mouse monoclonal IgGs labeled with $^{125}I$, buffer, proteins, stabilizing and preserving agents; maximum radioactivity = 496 kBq (13.4 $\mu$Ci) at the calibration date | 21 ml |
| standard 0 made up of a buffer, proteins and preserving agents | 30 ml |
| standards 1-4 containing the antigen 90 KD at the respective concentrations of 5-10-20-40 U/ml, HBsAg- and HIV-1-negative human serum, buffer, proteins and preserving agents | 1 ml |

The material mentioned above has been employed for analysing blood samples coming from the following subjects:
- 65 control subjects (normal subjects)
- 80 seronegative homosexuals exposed to the risk of AIDS
- 72 asymptomatic seropositive subjects
- 39 subjects suffering from the AIDS-Related Complex (ARC),
- 41 subjects suffering from AIDS.

The blood samples were subjected to centrifugation and the sera were separated and stored at −30° C.

At the moment of the analysis, the samples were thawed and diluted 1:100 with the "zero" standard (10 $\mu$l of the sample+990 $\mu$l of the zero standard) and all reactants had been conditioned at room temperature (20°-25° C.). Employing 20-well plastic reaction plates, the wells were identified for carrying out the assay of the standard and of the samples at least in duplicate. The standard 0 (100 $\mu$l) was distributed in all wells. The standards 0-4 (100 $\mu$l) and samples diluted (100 $\mu$l) were distributed in the respective wells. A small bead was put into each well. The wells were covered with a self-adhesive paper for preventing the sample from evaporating. The reaction plates were stirred mildly in order to remove any possible air bubbles, and keeping carefully the small beads completely covered.

The reaction plates were incubated for one hour at 37° C. At the end of the incubation, the self-adhesive paper was removed and the liquid was aspirated. Each well and the small bead contained therein were repeatedly washed with a total volume of 15 ml of deionized water by suction and automatic washing devices of known type.

100 μl of $^{125}$I-labeled SP-2 were put into each well. The plates were again incubated at 37° C. for one hour. At the end of incubation, each small bead was transferred from a well to a tube by overturning the well. The radioactivity of each small bead was measured with a gamma counter.

The average value of the countings has been evaluated for each set of 3 test-tubes, after subtracting the value of the background. Standard curves were plotted on linear axes, representing the average cpm as the ordinates for each standard and the corresponding 90 KD antigen concentrations as the abscissas. The 90 KD antigen concentrations as U/ml were then read directly off the standard curve.

The threshold value for distinguishing the normal subjects from the pathological subjects was set forth at 11 U/ml. Therefore values higher than 11 U/ml are considered as positive.

The proportion of anti-HIV seronegative subjects at risk of HIV infection with elevated 90 KD antigen levels in the blood is higher (27%) with respect to the normal control population (5%). On the contrary, as shown in the table 1, 43% of the asymptomatic seropositive subjects, 71% of the subjects suffering from ARC and 94% of the subjects suffering from AIDS showed 90K antigen levels in the blood higher than the normal level.

TABLE 1

| 90 KD antigen in different classes of subjects | | |
|---|---|---|
| | positive/total subjects | (%) | 90K U/ml |
| Control subjects | 9/170 | 5 | 5.5 ± 3.3 |
| seronegative subjects exposed to the risk of AIDS | 35/130 | 27 | 11.8 ± 14.5 |
| seropositive asymptomatic subjects | 47/108 | 43 | 14.9 ± 6.9 |
| ARC | 40/56 | 71 | 22.2 ± 14.3 |
| AIDS | 52/55 | 94 | 23.1 ± 11.2 |

Such data point out that the evolution of the disease, passing through the asymptomatic anti-HIV seropositive stage, the ARC and evident AIDS stages, is associated with a progressive and significative increase of the 90K antigen level in the blood.

These results have also confirmed by the correlation observed between the 90 KD antigen levels in the blood and the sub-population of the CD4 lymphocytes, whose decrease in peripheral blood is a marker of the progression of the disease. More particularly, high levels of the 90 KD antigen in the blood turned out to be closely correlated (p less than $10^{-6}$) to a low CD4 countings. The advantage of 90 KD the antigen assay with respect to the counting of the lymphocytes CD4 consists in that the increase of the 90 KD antigen level precedes the start of the decrease in the CD4 lymphocytes. Indeed, by the time a remarkable decrease of the CD4 lymphocytes occurs, the damage to the immunosystem is irreversible.

I claim:

1. A method for in vitro immunoassaying an antigen from biological fluids or tissues, said antigen being present in individuals infected with the AIDS virus, said antigen being of cytoplasmic origin and being recognized by an SP-2 monoclonal antibody produced by a hybridoma cell line deposited at the Collection Nationale de Cultures de Microorganismes, Accession No. I-1083, said method comprising the steps of:
    (a) taking a sample of biological fluid or tissue from a person;
    (b) contacting said biological fluids or tissues with said SP-2 monoclonal antibody;
    (c) removing an amount of said SP-2 monoclonal antibody not binding with said antigen; and
    (d) determining the amount of said SP-2 monoclonal antibody bound with said antigen utilizing at least one revealing system selected from the group consisting of enzyme, radioisotope, and chemiluminescent labels.

2. The method according to claim 1, wherein said biological tissue is blood.

3. The method according to claim 1, wherein said antigen is a cytoplasmic protein.